United States Patent
Stoop et al.

(10) Patent No.: US 6,901,291 B2
(45) Date of Patent: May 31, 2005

(54) DISTINGUISHING VALID AND INVALID CARDIAC SENSES

(75) Inventors: Gustaaf A. P. Stoop, Dieren (NL); Peter Van Dam, Doesburg (NL); Mattias Rouw, Arnhem (NL)

(73) Assignee: Medtronic, Inc., Minneapolis, MN (US)

( * ) Notice: Subject to any disclaimer, the term of this patent is extended or adjusted under 35 U.S.C. 154(b) by 487 days.

(21) Appl. No.: 09/994,873

(22) Filed: Nov. 28, 2001

(65) Prior Publication Data

US 2002/0128688 A1 Sep. 12, 2002

Related U.S. Application Data

(60) Provisional application No. 60/250,514, filed on Dec. 4, 2000.

(51) Int. Cl.[7] .............................................. A61N 1/362
(52) U.S. Cl. ........................................................ 607/27
(58) Field of Search ........................ 607/4, 5, 9, 11–14, 607/27, 28; 128/898

(56) References Cited

U.S. PATENT DOCUMENTS

| | | |
|---|---|---|
| 3,972,334 A | 8/1976 | Wickam |
| 4,129,133 A | 12/1978 | Irnich et al. |
| 4,316,472 A | 2/1982 | Mirowski et al. |
| 4,375,817 A | 3/1983 | Engle et al. |
| 4,379,459 A | 4/1983 | Stein |
| 4,384,585 A | 5/1983 | Zipes |
| 4,476,868 A | 10/1984 | Thompson et al. |
| 4,556,063 A | 12/1985 | Thompson et al. |
| 4,608,985 A | 9/1986 | Crish et al. |
| 4,727,877 A | 3/1988 | Kallok |
| 4,800,883 A | 1/1989 | Winstrom |
| 4,821,723 A | 4/1989 | Baker et al. |
| 4,928,688 A | 5/1990 | Mower |
| 4,949,719 A | 8/1990 | Pless |
| 4,953,551 A | 9/1990 | Mehra |
| 5,117,824 A | 6/1992 | Keimel |
| 5,131,388 A | 7/1992 | Pless |
| 5,144,943 A | 9/1992 | Luttrell et al. |
| 5,158,078 A | 10/1992 | Bennett et al. |
| 5,163,427 A | 11/1992 | Keimel |
| 5,257,621 A * | 11/1993 | Bardy et al. .................... 607/5 |
| 5,269,298 A | 12/1993 | Adams et al. |
| 5,312,453 A | 5/1994 | Shelton et al. |
| 5,314,430 A | 5/1994 | Bardy |
| 5,354,316 A | 10/1994 | Keimel |
| 5,545,186 A | 8/1996 | Olsan |
| 5,800,465 A | 9/1998 | Thompson et al. |
| 5,902,324 A * | 5/1999 | Thompson et al. ............ 607/9 |
| 5,944,743 A | 8/1999 | Janssens |
| 6,070,101 A | 5/2000 | Struble et al. |
| 6,081,748 A | 6/2000 | Struble et al. |
| 6,088,614 A | 7/2000 | Swanson |

FOREIGN PATENT DOCUMENTS

| | | |
|---|---|---|
| EP | 0429025 A2 | 11/1989 |
| EP | 0707866 A2 | 4/1996 |

OTHER PUBLICATIONS

PCT International Search Report, PCT/US/02/09895 (Aug. 26, 2002).

* cited by examiner

*Primary Examiner*—George Manuel
(74) *Attorney, Agent, or Firm*—Girma Wolde-Michael; Daniel G. Chapik

(57) ABSTRACT

Systems and methods for distinguishing a valid sensed cardiac signal from an invalid signal, such as a myopotential. In one embodiment, sensing an electrical signal with one electrode causes a timing window to commence. When the electrical signal is sensed by another electrode in the timing window, the sense is deemed valid. When the electrical signal is not sensed by the other electrode in the timing window, the sense is deemed invalid. Therapy may be adjusted when an inordinate number of senses are invalid.

53 Claims, 13 Drawing Sheets

DISTINGUISHING VALID AND INVALID CARDIAC SENSES

This application claims priority from U.S. Provisional Application Ser. No. 60/250,514, filed Dec. 4, 2000, the entire content of which is incorporated herein by reference.

FIELD OF THE INVENTION

The invention relates to cardiac pacing systems, and more particularly to multiple-chamber cardiac pacing systems.

BACKGROUND

In multi-chamber pacing of a heart, an implanted medical device such as a pacemaker delivers pacing pulses to two or more chambers of the heart. The timing of the pacing pulses is important. Many patients benefit from having chambers paced in a particular order with a delay between the respective pacing pulses.

A patient who has undergone an ablate and pace therapy presents an example of a patient that may benefit from the timing of multi-chamber pacing pulses. Ablate and pace therapy is often used with patients having symptomatic drug-refractory atrial fibrillation. In many patients, ablate and pace therapy has been found to reduce the frequency of atrial fibrillation conducted to the ventricle and improve the quality of life. Ablate and pace therapy includes a surgical procedure in which a surgeon surgically ablates the atrio-ventricular junction of the heart and implants a pacing system. The implanted pacing system supplants, to some extent, the heart's natural pacing system.

The dual-chamber pacing system includes a right ventricular pacing lead positioned conventionally in the right ventricle of the heart and a left ventricular pacing lead positioned via the coronary sinus in a cardiac vein, such as the middle or great cardiac vein. The pacing leads include electrodes that sense electrical activity. These "senses" may be indicative of cardiac activity such as ventricular contraction. The pacing electrodes also supply paces to the heart, i.e., electrical impulses generated by the implanted pacemaker that cause the heart to contract.

The right ventricular (RV) pace/sense electrode can deliver paces to the right ventricle and the left ventricular (LV) pace/sense electrode deliver paces to the left ventricle. Although the paces to the ventricles may be delivered simultaneously, patients may benefit from having one ventricle paced before the other.

On some occasions, the ventricles may contract intrinsically, i.e., in response to an activation generated by the heart instead of by the pacemaker. The pacing system senses intrinsic contractions via the RV and LV pace/sense electrodes.

Some senses may not be valid. Senses via the LV pace/sense electrode, in particular, are susceptible to being invalid. In other words, the LV pace/sense electrode is susceptible to detection of signals that may be mistaken by the pacemaker for the electrical signals that accompany a ventricular contraction. An invalid sense may be caused by a far field P-wave, i.e., the electrical activity of the atria sensed by a ventricular lead. Another invalid sense may be caused by myopotentials, i.e., electrical signals from muscles other than the heart. These senses are invalid because they accompany activity other than ventricular activity.

In some forms of cardiac therapy, the pacemaker applies therapy in response to sensed cardiac activity. Such therapies may depend upon the ability of the pacemaker to receive valid senses. If some or all of the senses are invalid and the pacemaker cannot discriminate between valid and invalid senses, the pacemaker may apply therapy that is not needed, or may apply needed therapy inappropriately.

Multiple-chamber pacing systems are known in the art, including systems that pace and sense the right ventricle and the left ventricle. In addition, techniques associated with cardiac tissue ablation are known in the art, as are techniques for generating pulses to block orthodromic pulses. Examples of these techniques and/or devices may be found in the issued U.S. Patents listed in Table 1 below.

TABLE 1

| U.S. Pat. No. | Inventor | Issue Date |
|---|---|---|
| 6,088,614 | Swanson | Jul. 11, 2000 |
| 6,081,748 | Struble et al. | Jun. 27, 2000 |
| 6,070,101 | Struble et al. | May 30, 2000 |
| 5,944,743 | Janssens | Aug. 31, 1999 |
| 4,928,688 | Mower | May 29, 1990 |
| 4,608,985 | Crish et al. | Sep. 02, 1986 |

All patents listed in Table 1 above are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the techniques of the present invention.

SUMMARY OF THE INVENTION

The present invention has certain objects. That is, various embodiments of the present invention provide solutions to one or more problems existing in the prior art with respect to multiple chamber cardiac pacemakers in general, and bi-ventricular cardiac pacemakers in particular. These problems include, for example, an inability to distinguish a valid cardiac sense from an invalid sense, and an inability to recognize when a pace/sense electrode is detecting an inordinate number of invalid senses. Various embodiments of the present invention have the object of solving at least one of the foregoing problems.

It is an object of the invention to distinguish valid cardiac senses from invalid senses. Because cardiac senses trigger some therapies, appropriate delivery of the therapies may depend upon the ability of the pacemaker to recognize valid senses. Invalid senses may cause the pacemaker to apply therapy that is not needed, or to apply needed therapy inappropriately. Recognizing invalid senses, therefore, reduces the risk that the pacemaker will apply therapy that is not needed, or apply needed therapy inappropriately.

It is a further object of the invention to monitor senses for invalidity and to adjust the therapy when too many invalid senses may result in too many "false alarms." A therapy that is triggered by a sense may not beneficial or may be harmful when triggered by one or more invalid senses. It is an object of the invention to take action, such as suspending therapy triggered by senses, when too many senses are invalid.

It is a further object of the invention to distinguish valid cardiac senses from invalid senses using techniques that can be adapted to any patient. Because of the differences in patients' hearts and the differences in placements of pace/sense electrodes, susceptibility to invalid senses may differ from patient to patient. The invention should be customizable to the patient, and should not interfere with other pacing functions.

Various embodiments of the invention may possess one or more features capable of fulfilling the above objects. In general, the invention distinguishes valid senses from invalid senses. In an exemplary implementation, in the context of bi-ventricular pacing, the invention distinguishes valid LV senses from invalid LV senses. The invention is not limited to the context of bi-ventricular pacing, however, and may find application in other types of multi-chamber pacing.

The invention is directed, in one embodiment, to a method in which a pacemaker senses an electrical signal with a first electrode and commences a timing window called an intrinsic inhibition window. If the pacemaker fails to sense the electrical signal in the timing window with a second electrode, the pacemaker records the electrical signal as an invalid sense. Alternatively, if the pacemaker senses the electrical signal in the timing window with a second electrode, the pacemaker records the electrical signal as a valid sense.

In the context of bi-ventricular pacing, a sense via the LV pace/sense electrode causes an intrinsic inhibition window to commence. If the sense is a valid sense, i.e., indicative of electrical activity accompanying ventricular contraction, then the same electrical activity is expected to be sensed via the RV pace/sense electrode before the intrinsic inhibition window expires. When the RV pace/sense electrode senses the electrical activity in the intrinsic inhibition window, the sense is valid, but when the RV pace/sense electrode fails to sense the electrical activity in the intrinsic inhibition window, the sense is invalid.

The invention may also be embodied as a system that includes a first electrode for placement proximal to a heart and a second electrode disposed proximal to the heart. The first and second electrodes may be the LV pace/sense electrode and the RV pace/sense electrode, but the invention is not limited to the bi-ventricular context. A controller in the system, such as a microprocessor, senses an electrical signal with the first electrode and commences a timing window. The controller records the electrical signal as an invalid sense when the second electrode fails to sense the electrical signal in the timing window.

The duration of timing windows may vary from patient to patient. Accordingly, the invention may further be embodied as a method for selecting a timing window for a patient. In a first monitoring period, the pacemaker senses at least one electrical signal with a first electrode, commences a timing window having a first duration and records the electrical signal as an invalid sense when a second electrode fails to sense the electrical signal in the timing window. In a second monitoring period, the pacemaker performs the same steps except that the timing window has a second duration. The steps may be repeated with additional monitoring periods and timing windows of different durations. After data for various monitoring periods are accumulated, the pacemaker selects a timing window that that is wide enough to distinguish valid senses from invalid senses.

The invention offers one or more advantages. Valid cardiac senses can easily be distinguished from invalid senses. Valid senses are detected by two electrodes within a timing window, and invalid senses are not. The techniques of the invention may be applied to any of a number of pace/sense electrodes disposed proximal to the heart, although the invention will be described in detail in the context of bi-ventricular pacing.

Use of a timing window is also flexible, can be customized to the patient, does not interfere with other pacing functions and is not computationally demanding. Morphological analysis may also be used to supplement or supplant use of the timing window. Furthermore, data pertaining to valid and invalid senses may be used to automatically regulate pacemaker therapies that rely on valid senses.

The details of one or more embodiments of the invention are set forth in the accompanying drawings and the description below. Other features, objects, and advantages of the invention will be apparent from the description and drawings, and from the claims.

DETAILED DESCRIPTION OF THE PREFERRED EMBODIMENTS

In the following detailed description of the preferred embodiments, reference is made to the accompanying drawings that form a part hereof, and in which are shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
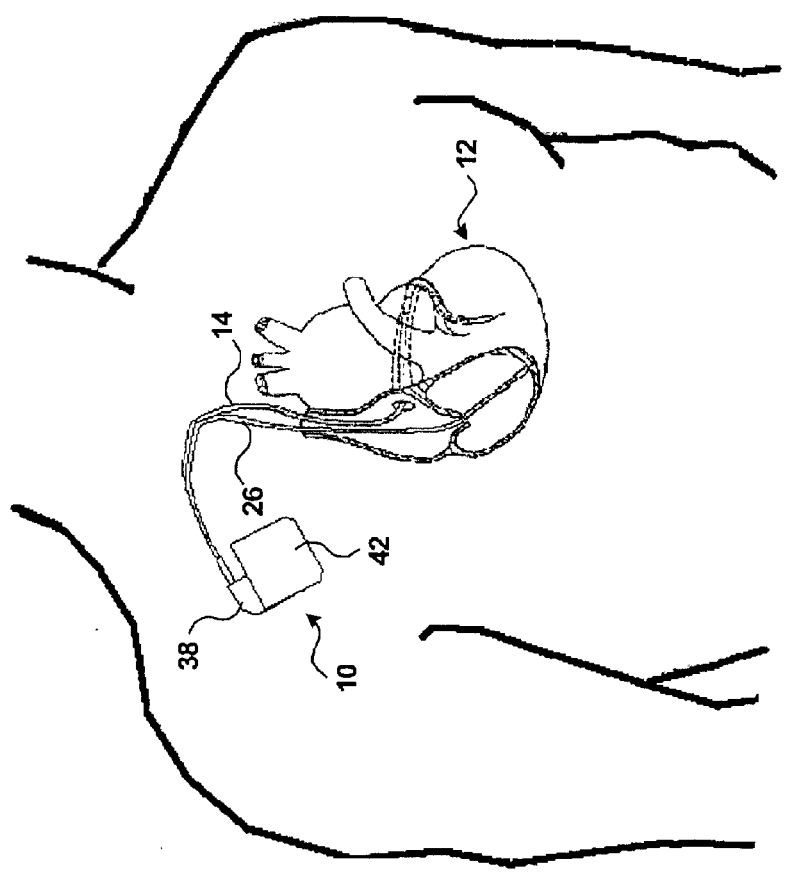
FIG. 1 is a schematic view of an exemplary implantable medical device.

FIG. 1 is a simplified schematic view of pacemaker 10, which is one embodiment of an implantable medical device of the present invention. Pacemaker 10 shown in FIG. 1 comprises at least one of pacing and sensing leads 14 and 26 attached to connector module 38 of hermetically sealed housing 42 and implanted near human or mammalian heart 12. Pacing and sensing leads 14 and 26 sense electrical signals attendant to the depolarization and repolarization of the heart 12, and further provide pacing pulses for causing depolarization of cardiac tissue in the vicinity of the distal ends thereof. Leads 14 and 26 may have unipolar or bipolar electrodes disposed thereon, as is well known in the art. Examples of pacemaker 10 include implantable cardiac pacemakers disclosed in U.S. Pat. No. 5,158,078 to Bennett et al., U.S. Pat. No. 5,312,453 to Shelton et al., or U.S. Pat. No. 5,144,949 to Olson, all hereby incorporated by reference herein, each in its respective entirety.

Figure 2:
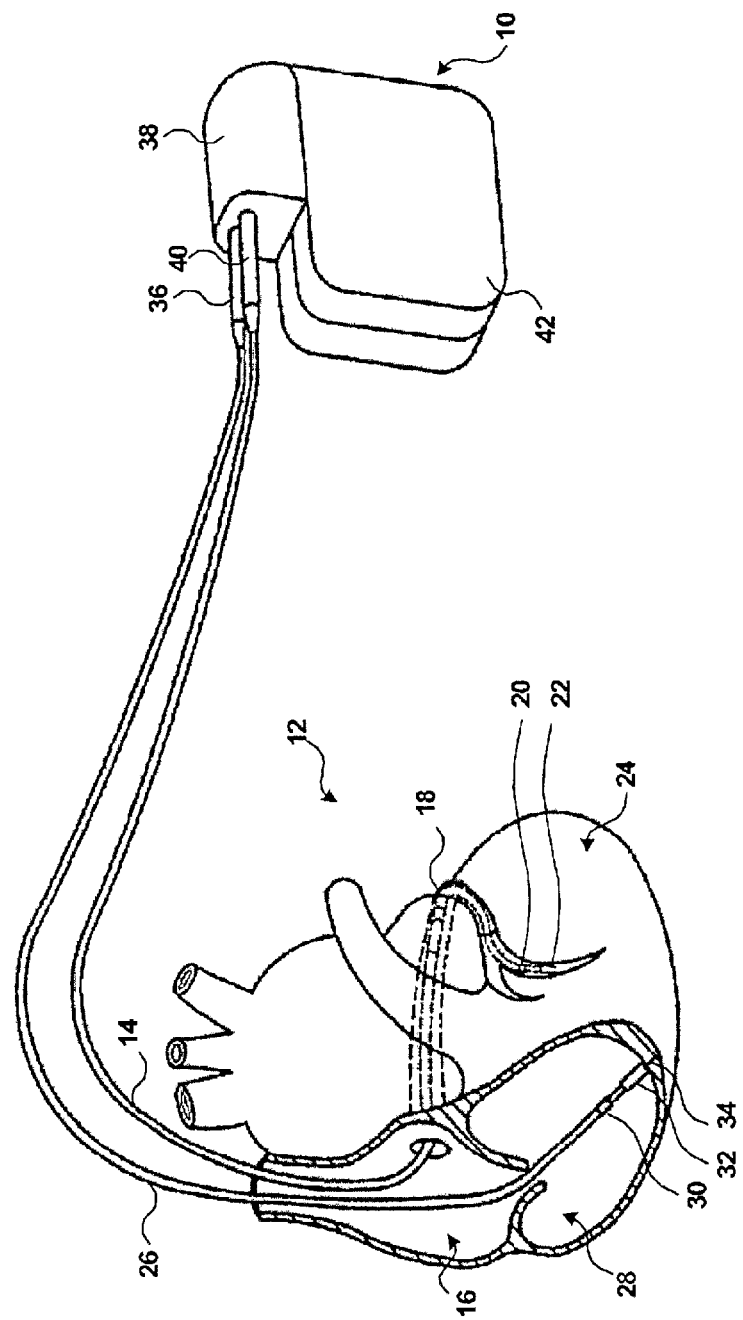
FIG. 2 shows an exemplary implantable medical device located in and near a heart.

FIG. 2 is a schematic representation of an exemplary implanted, two-channel cardiac pacemaker 10 in which the invention may be practiced. Pacemaker 10 is shown in conjunction with a human heart 12. Bipolar, endocardial left ventricular (LV) coronary sinus lead 14 is passed through a vein into the right atrium 16 of heart 12, into the coronary sinus 18 and then inferiorly in the great vein and cardiac veins extending from coronary sinus 18 to extend the distal ring pace/sense electrodes 20 and 22 alongside the LV chamber 24. The distal end of LV coronary sinus lead 14 positions ring electrodes 20 and 22 optimally with respect to the adjacent wall of left ventricle 24. Bipolar, endocardial right ventricular (RV) lead 26 is passed through the vein into right atrium 16 and into the right ventricle 28 where its distal ring and tip pace/sense electrodes 30 and 32 are fixed in place in the apex or in the interventricular septum by a distal attachment mechanism 34.

Pace/sense electrodes 20, 22, 30 and 32 sense electrical signals attendant to the depolarization and repolarization of heart 12. The electrical signals are conducted to pacemaker 10 via leads 14 and 26. Pace/sense electrodes 20, 22, 30 and 32 further deliver pacing pulses for causing depolarization of cardiac tissue in the vicinity of the distal ends thereof. The pacing pulses are generated by pacemaker 10 and are transmitted to pace/sense electrodes 20, 22, 30 and 32 via leads 14 and 26.

RV lead 26 is formed with an in-line connector 36 fitting into a bipolar bore of pacemaker connector block 38. RV lead 26 includes a pair of electrically insulated conductors that couple distal tip pace/sense electrode 32 and proximal pace/sense ring electrode 30 to pacemaker 14. LV coronary sinus lead 14 is formed with an in-line connector 40 fitting into a bipolar bore of pacemaker connector block 38. LV coronary sinus lead 14 couples distal ring pace/sense electrode 22 and proximal pace/sense ring electrode 20 to pacemaker 14.

When a pacing pulse is delivered, or when intrinsic activity is sensed, pacemaker 10 commences a ventricular escape interval. The ventricular escape interval is typically timed from the RV paced and sensed events, but it can be timed from the LV paced and sensed events in appropriate circumstances. In the discussion that follows, it is assumed that RV events are used as references to control timing.

In some instances, a patient's ventricles may exhibit "intrinsic activity," i.e., the ventricles may contract without pacing. The electrical activity accompanying the contraction is sensed by one or more electrodes, and is a sensed event. Ideally, when the intrinsic activity is sensed, the pending ventricular escape interval ends and a new ventricular escape interval begins. As will be discussed in more detail below, however, not all sensed events represent ventricular contractions. Accordingly, it is desirable to avoid causing pacemaker 10 to commence a new ventricular escape interval due to invalid sensed events.

If the ventricular escape interval times out or expires, then a pace pulse is delivered across the RV pace/sense electrodes 30 and 32. A pace pulse may also be delivered across LV pace/sense electrodes 20 and 22. The LV pace pulse and the RV pace pulse need not be delivered simultaneously. Some patients may benefit, for example, when the LV pace pulse is delivered, and the RV pace pulse is delivered following a delay. This delay is referred to as a "positive LV-RV delay." With a positive LV-RV delay, RV paced and sensed events are used for timing, even though the LV pace pulse is delivered before the RV pace pulse. Other patients, however, may benefit from a "negative LV-RV delay," in which the RV pace pulse comes before the LV pace pulse.

When a patient benefits from a positive LV-RV delay, then intrinsic activity that causes the right ventricle to beat first is undesirable for that patient. Similarly, for a patient that benefits from a negative LV-RV delay, intrinsic activity that causes the left ventricle to beat first is undesirable. An antidromic event occurs when the ventricles contract out of order. When an antidromic event is detected, pacemaker 10 may compensate by pacing the ventricle that ought to have contracted first. As a result, the ventricles contract nearly simultaneously. Near-simultaneous contraction is generally better for the patient than having the ventricles contract intrinsically out of order.

In some patients, the signals detected by LV pace/sense electrodes 20 and 22 are not valid, i.e., the signals are not indicative of LV contraction. Therapies such as compensation for antidromic events rely upon valid senses of ventricular activity. If factors other than ventricular activity result in a signal that is mistaken for an LV contraction, the therapy may be applied inappropriately.

A far field P-wave is one example of activity that may be mistaken for an electrical signal that accompanies a ventricular contraction. A far field P-wave indicates electrical activity in one or more atria measured by a ventricular lead. Similarly, myopotentials, which are electrical signals from muscles other than the heart, may be mistaken for the electrical signals that accompany a ventricular contraction. In some patients, LV pace/sense electrodes 20 and 22 are more susceptible to detection of invalid signals than RV pace/sense electrodes 30 and 32, so signals detected by LV pace/sense electrodes 20 and 22 should be examined more carefully for validity.

The invention presents techniques for detecting and responding to signals detected by LV pace/sense electrodes 20 and 22. In general, invalid signals are ignored and are not allowed to disrupt pacemaker timing. Valid signals, on the other hand, may result in resetting of pacemaker timing. In some circumstances, the timing of a signal detected by LV pace/sense electrodes 20 and 22 is such that it is not important to categorize the signal as valid or invalid.

The pacing system shown in FIG. 2 is exemplary. The invention is not limited to the electrode placements shown in FIG. 2. LV pace/sense electrodes 20 and 22, for example, may be located at a site other than coronary sinus 18. RV pace/sense electrodes 30 and 32 may be epicardial, rather than endocardial as shown in FIG. 2. The pacing system may also include alternate or additional leads that deploy electrodes proximal to the atria for sensing or pacing.

Furthermore, the invention is not limited to the bipolar ventricular lead systems depicted in FIG. 2. The invention may be employed with unipolar lead systems that employ a single pace/sense electrode in the depicted positions proximal to right ventricle 24 and left ventricle 28. Unipolar electrodes may cooperate with a remote electrode formed as part of the outer surface of the hermetically sealed housing 42 of pacemaker 10.

Figure 3:
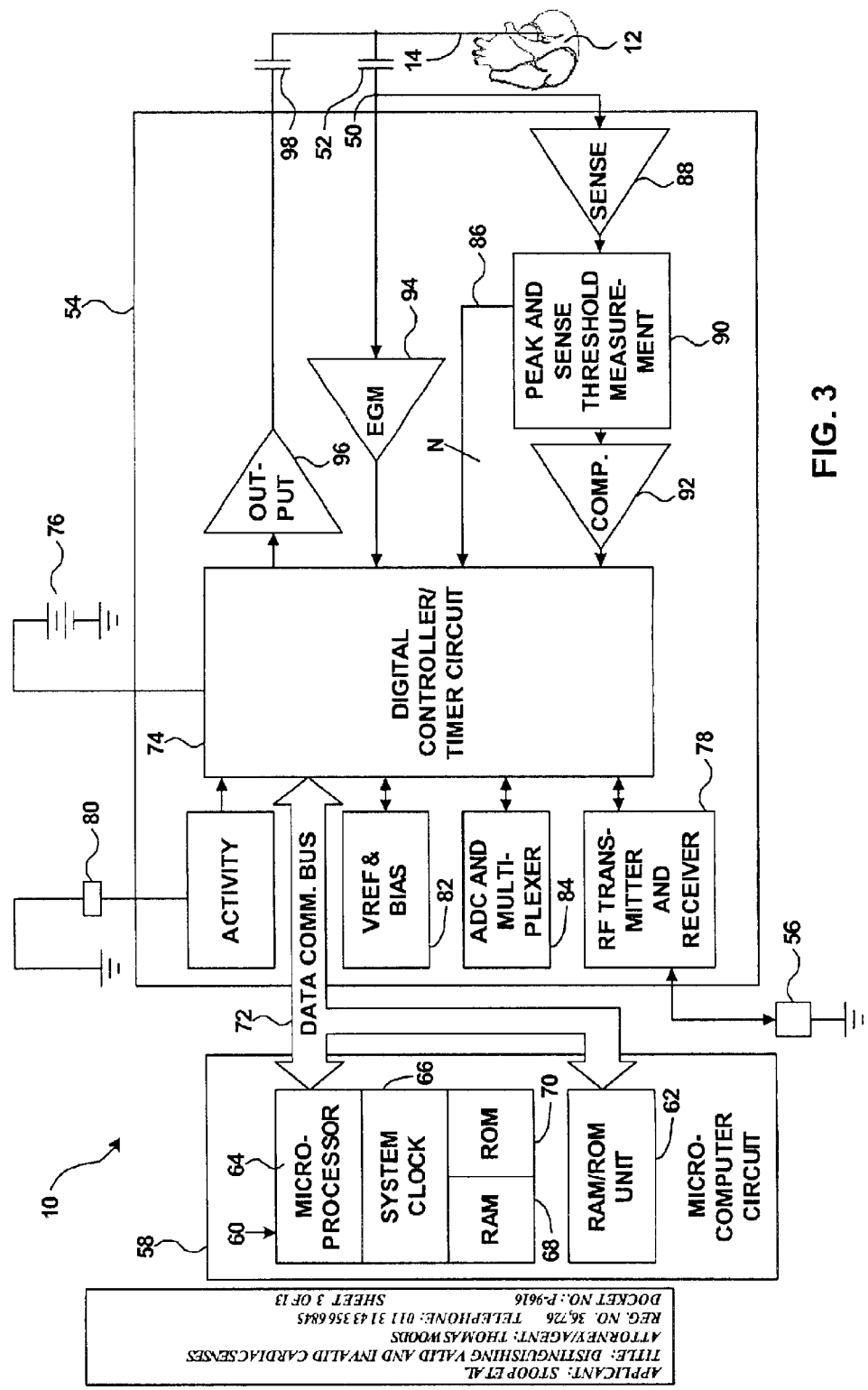
FIG. 3 is a block diagram illustrating the constituent components of the implantable medical device of FIGS. 1 and 2.

FIG. 3 shows a block diagram illustrating the constituent components of pacemaker 10 in accordance with one embodiment of the present invention. Pacemaker 10 is a pacemaker having a microprocessor-based architecture. Pacemaker 10 is shown as including activity sensor or accelerometer 80, which is preferably a piezoceramic accelerometer bonded to a hybrid circuit located inside housing 42 (shown in FIGS. 1 and 2). Activity sensor 80 typically (although not necessarily) provides a sensor output that varies as a function of a measured parameter relating to a patient's metabolic requirements. For the sake of convenience, pacemaker 10 in FIG. 3 is shown with lead 14 only connected thereto. However, it is understood that similar circuitry and connections not explicitly shown in FIG. 3 apply to lead 26 (shown in FIGS. 1 and 2).

Pacemaker 10 in FIG. 3 is most preferably programmable by means of an external programming unit (not shown in the figures). One such programmer is the commercially available Medtronic Model 9790 programmer, which is microprocessor-based and provides a series of encoded signals to pacemaker 10, typically through a programming head which transmits or telemeters radio-frequency (RF) encoded signals to pacemaker 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 14 is coupled to node 50 in pacemaker 10 through input capacitor 52. Activity sensor or accelerometer 80 is most preferably attached to a hybrid circuit located inside hermetically sealed housing 42 of pacemaker 10. The output signal provided by activity sensor 80 is coupled to input/output circuit 54. Input/output circuit 54 contains analog circuits for interfacing with heart 12, activity sensor 80, antenna 56 and circuits for the application of stimulating pulses to heart 12. The rate of heart 12 is controlled by software-implemented algorithms stored within microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board random access memory (RAM) 68 and read-only memory (ROM) 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of pacemaker 10 is not shown in the Figures.

Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, VREF and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of pacemaker 10 are coupled from microprocessor 64 via data bus 72 to digital controller/timer circuit 74, where digital timers and counters establish the overall escape interval of the pacemaker 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 14. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 86 to digital controller/timer circuit 74. An amplified sense amplifier signal is also provided to comparator/threshold detector 92. By way of example, sense amplifier 88 may correspond to that disclosed in U.S. Pat. No. 4,379,459 to Stein, hereby incorporated by reference herein in its entirety.

As noted above and as discussed in more detail below, signals received via lead 14 may be valid, in which the signals reflect a ventricular contraction, or invalid, in which the signals do not reflect a ventricular contraction. Sense amplifier 88, threshold measurement circuitry 90 and comparator/threshold detector 92 are generally unable to distinguish a valid signal from an invalid signal.

The electrogram signal provided by EGM amplifier 94 is employed when pacemaker 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides amplified pacing stimuli to patient's heart 12 through coupling capacitor 98 in response to a pacing trigger signal provided by digital controller/timer circuit 74 each time either (a) the escape interval times out, (b) an externally transmitted pacing command is received, or (c) in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of sense amplifier 88, output pulse generator 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 12.

In some preferred embodiments of the present invention, pacemaker 10 may operate in various non-rate-responsive modes. In other preferred embodiments of the present invention, pacemaker 10 may operate in various rate-responsive modes. Some embodiments of the present invention are capable of operating in both non-rate-responsive and rate-responsive modes. Moreover, in various embodiments of the present invention pacemaker 10 may be programmably configured to operate so that it varies the rate at which it delivers stimulating pulses to heart 12 in response to one or more selected sensor outputs being generated. Numerous pacemaker features and functions not explicitly mentioned herein may be incorporated into pacemaker 10 while remaining within the scope of the present invention.

The present invention is not limited in scope to any particular number of sensors, and is not limited to pacemakers comprising activity or pressure sensors only. Although the present invention is useful in multiple-chamber pacemakers, the present invention is not limited in scope to multiple-chamber pacemakers or to pacemakers having any particular number of sensors per lead. At least some embodiments of the present invention may be applied equally well in the contexts of single-, dual-, triple- or quadruple-chamber pacemakers or other types of pacemakers. See, for example, U.S. Pat. No. 5,800,465 to Thompson et al., hereby incorporated by reference herein in its entirety, as are all U.S. Patents referenced therein.

Pacemaker 10 may also be a pacemaker combined with a cardioverter and/or defibrillator. Various embodiments of the present invention may be practiced in conjunction with a pacemaker-cardioverter-defibrillator such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, and U.S. Pat. No. 4,821,723 to Baker et al., all hereby incorporated by reference herein, each in its respective entirety.

Figure 4:
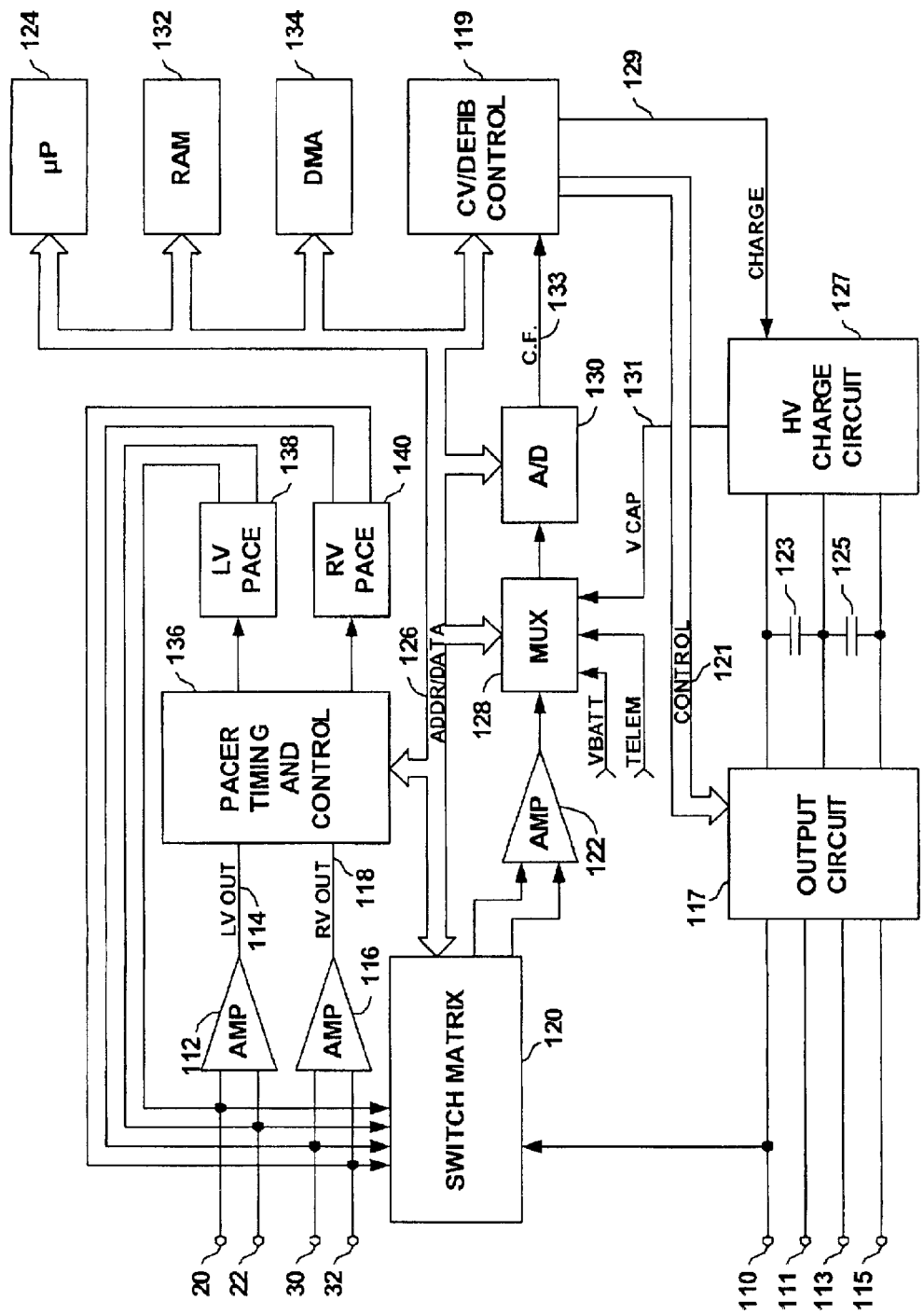
FIG. 4 is a functional schematic diagram of an exemplary embodiment of the implantable medical device of FIGS. 1 and 2.

FIG. 4 is a functional schematic diagram of one embodiment of pacemaker 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators that do not provide anti-tachycardia pacing therapies.

Pacemaker 10 is provided with an electrode system. Electrode 110 in FIG. 4 includes the uninsulated portion of housing 42 of pacemaker 10. Electrodes 110, 111, 113 and 115 are coupled to high voltage output circuit 117, which includes high voltage switches controlled by CV/defib control logic 119 via control bus 121. Switches disposed within circuit 117 determine which electrodes are employed and which electrodes are coupled to the positive and negative terminals of the capacitor bank (which includes capacitors 123 and 125) during delivery of defibrillation pulses.

Electrodes 20 and 22 are located on or in left ventricle 24 of the patient and are coupled to amplifier 112, which preferably takes the form of an automatic gain controlled amplifier providing an adjustable sensing threshold as a function of the measured R-wave amplitude. A signal is generated on LV out line 114 whenever the signal sensed between electrodes 20 and 22 exceeds the present sensing threshold.

As noted above, signals detected by LV pace/sense electrodes 20 and 22 may be indicative of LV contraction, but pace/sense electrodes 20 and 22 are also susceptible to detection of signals indicative of factors such as atrial activity or myopotentials. Signals indicative of LV contraction and signals indicative of other factors may exceed the present sensing threshold of amplifier 112, and may cause a signal to be generated on LV out line. Such a signal, called a left ventricular sense (LVS), may be valid or invalid. A valid LVS reflects a ventricular contraction, and an invalid LVS does not.

Electrodes 30 and 32 are located on or in right ventricle 28 of the patient and are coupled to amplifier 116, which preferably also takes the form of an automatic gain controlled amplifier providing an adjustable sensing threshold as a function of the measured R-wave amplitude. A signal is generated on RV out line 118 whenever the signal sensed between electrodes 30 and 32 exceeds the present sensing threshold. The general operation of amplifiers 112 and 116 may correspond to that disclosed in U.S. Pat. No. 5,117,824 to Keimel et al., hereby incorporated by reference herein in its entirety.

Switch matrix 120 is used to select which of the available electrodes are coupled to wide band (0.5–200 Hz) amplifier 122 for use in digital signal analysis. Selection of electrodes is controlled by microprocessor 124 via data/address bus 126, which selections may be varied as desired. Signals from the electrodes selected for coupling to band pass amplifier 122 are provided to multiplexer 128, and thereafter converted to multi-bit digital signals by A/D converter 130, for storage in random access memory 132 under control of direct memory access circuit 134. Microprocessor 124 may employ digital signal analysis techniques to characterize the digitized signals stored in random access memory 132 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 136 preferably includes programmable digital counters which control the basic time intervals associated with modes of pacing well known to the art. Circuitry 136 also preferably controls escape intervals associated with pacing. In the exemplary bi-ventricular pacing environment, pacer timing/control circuitry 136 controls the ventricular escape interval that is used to time pacing pulses delivered to the ventricles.

Intervals defined by pacing circuitry 136 may also include atrial pacing escape intervals, the refractory periods during which sensed P-waves and R-waves are ineffective to restart timing of the escape intervals and the pulse widths of the pacing pulses. The durations of these intervals are determined by microprocessor 124, in response to stored data in memory 132 and are communicated to pacing circuitry 136 via address/data bus 126. Pacer circuitry 136 also determines the amplitude of the cardiac pacing pulses under control of microprocessor 124.

During pacing, escape interval counters within pacer timing/control circuitry 136 may be reset upon sensing of R-waves as indicated by a signals on lines 114 and 118, as will be described in more detail below. In accordance with the selected mode of pacing, pacer timing/control circuitry 136 triggers generation of pacing pulses by pacer output circuitry 138 and 140, which are coupled to electrodes 20, 22, 30 and 32. Escape interval counters may also be reset on generation of pacing pulses and thereby control the basic timing of cardiac pacing functions. The durations of the intervals defined by escape interval timers are determined by microprocessor 124 via data/address bus 126. The value of the count present in the escape interval counters when reset by sensed R-waves may be used to measure the durations of parameters such as R-R intervals, which measurements are stored in memory 132.

Microprocessor 124 most preferably operates as an interrupt driven device, and is responsive to interrupts from pacer timing/control circuitry 136 corresponding to the occurrence of sensed R-waves and corresponding to the generation of cardiac pacing pulses. Those interrupts are provided via data/address bus 126. Any necessary mathematical calculations to be performed by microprocessor 124 and any updating of the values or intervals controlled by pacer timing/control circuitry 136 take place following such interrupts.

In the event that generation of a cardioversion or defibrillation pulse is required, microprocessor 124 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 124 activates cardioversion/defibrillation control circuitry 119, which initiates charging of the high voltage capacitors 123 and 125 via charging circuit 127, under the control of high voltage charging control line 129. The voltage on the high voltage capacitors 123 and 125 is monitored via VCAP line 131, which is passed through multiplexer 128 and in response to reaching a predetermined value set by microprocessor 124, results in generation of a logic signal on Cap Full (CF) line 133 to terminate charging. Thereafter, timing of the delivery of the defibrillation or cardioversion pulse is controlled by pacer timing/control circuitry 136. Following delivery of the fibrillation or tachycardia therapy microprocessor 124 returns the device to cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 4, delivery of cardioversion or defibrillation pulses is accomplished by output circuit 117 under the control of control circuitry 119 via control bus 121. Output circuit 117 determines whether a monophasic or biphasic pulse is delivered, the polarity of the electrodes and which electrodes are involved in delivery of the pulse. Output circuit 117 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the U.S. Pat. No. 4,953,551 to Mehra et al. and in U.S. Pat. No. 4,727,877 to Kallok, hereby incorporated by reference herein in their entireties.

An example of circuitry that may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

The embodiment shown in FIG. 4 is merely exemplary, and is intended to provide additional details pertaining to the exemplary embodiment shown in FIGS. 1 and 2. The embodiment shown in FIG. 4 may be modified to include additional features, or may be adapted to other embodiments. For example, the embodiment in FIG. 4 may be modified for an implanted medical device having electrodes mounted on a lead (not shown in FIGS. 1–4) positioned proximal to right atrium 16. Such electrodes may be coupled to a P-wave amplifier (not shown in FIG. 4) that, like amplifiers 112 an 116, provides an adjustable sensing threshold as a function of a measured P-wave amplitude. The embodiment shown in FIG. 4 may further be modified to detect activity in or near the left atrium of the patient.

In addition, the embodiment shown in FIG. 4 can be adapted to provide additional therapy, such as detection or pacing of tachycardia. Accordingly, microprocessor 124 may perform mathematical calculations to carry out tachyarrhythmia detection algorithms known in the art. The present invention is believed to find wide application to any form of implantable electrical device for use in conjunction with electrical leads. The invention presents techniques for recognizing valid and invalid signals detected by electrodes such as LV pace/sense electrodes 20 and 22. The invention further presents techniques for responding to the detection of valid and invalid signals.

Figure 5:
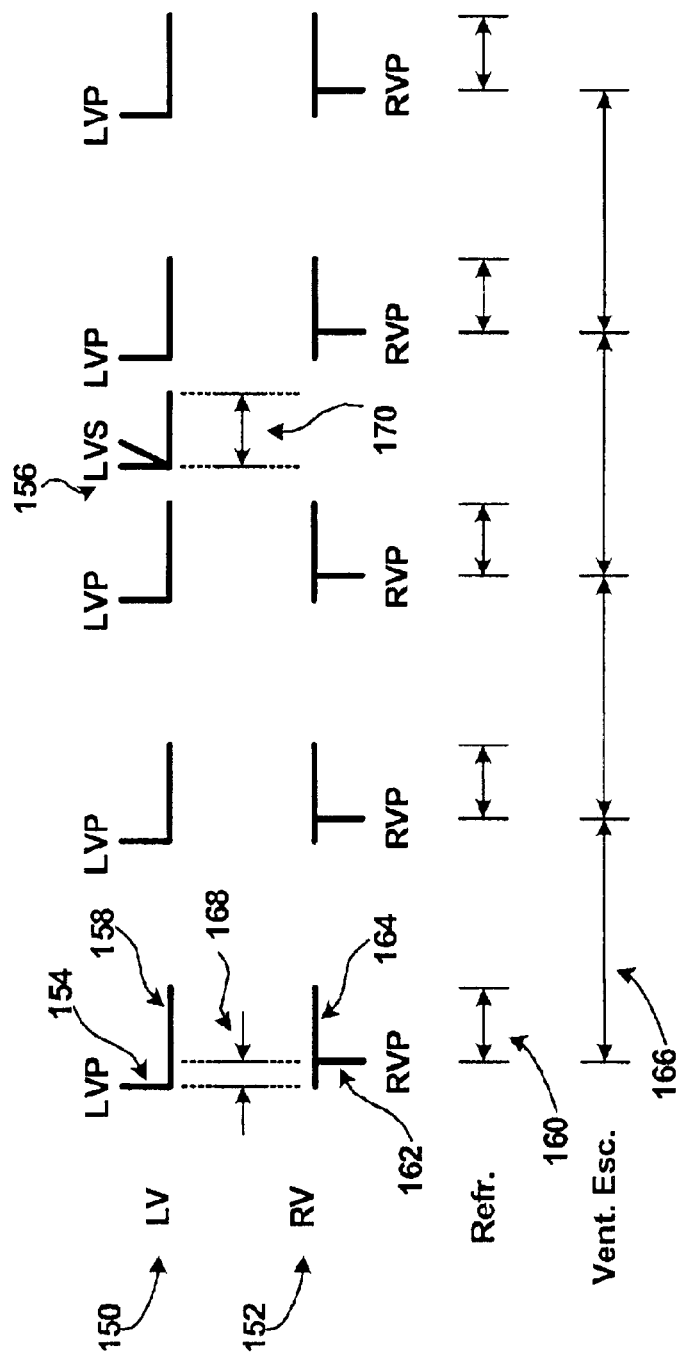
FIG. 5 is a timing diagram that illustrates a technique for recognition of an invalid sense.

FIG. 5 is a timing diagram that illustrates a technique for recognition of an invalid signal. FIG. 5 includes two graphs 150, 152 drawn to the same time scale. Upper graph 150 represents LV activity and lower graph 152 represents RV activity. LV activity includes paces delivered to left ventricle 24 as well as LVS's. A delivered left ventricular pace (LVP) is denoted by a vertical line, such as that identified by reference numeral 154. An LVS is denoted by a V-shaped symbol, such as that identified by reference numeral 156.

An LVS represents sensed, as opposed to paced, activity. While paced activity results in ventricular contraction, an LVS may or may not be indicative of ventricular contraction. A valid LVS reflects ventricular contraction and an invalid LVS does not.

A horizontal timing line, such as that identified by reference numeral 158, helps visualize an important interval called the refractory period. An exemplary refractory period is identified by reference numeral 160. Horizontal timing line 158 ends when refractory period 160 ends.

The refractory period is a period of time in which an electrode or sensing circuit inhibits detection of signals. The purpose of a refractory period is to prevent detection of signals, such as after-potentials, that accompany paced or intrinsic contractions. As will be described below, RV events are used as references to control timing. Consequently, refractory period 160 is controlled by RV activity.

RV activity in lower graph 152 includes paced events, such as the vertical line identified by reference numeral 162. A signal indicating a right ventricular sense (RVS) is denoted by a V-shaped symbol, but FIG. 5 includes no RSV's. A horizontal timing line, such as that identified by reference numeral 164, helps visualize the end of the refractory period.

RV paced and sensed events are used for timing. A ventricular escape interval, such as the interval denoted by reference numeral 166, represents the planned time between RV paces. As shown in FIG. 5, a right ventricular pace (RVP) occurs at the conclusion of an escape interval.

Escape intervals and refractory periods may vary from time to time and from patient to patient. For example, a patient at rest may have the ventricles paced sixty times per minute, with a ventricular escape interval of one second. When activity sensor 80 detects a change in the patient's metabolic requirements, however, the number of paces per minute may change and accordingly the ventricular escape interval may change.

FIG. 5 further illustrates an exemplary positive LV-RV delay 168. RV and sensed events are used for timing, but the LVP precedes the RVP. The interval by which the LVP precedes the RVP is a positive LV-RV delay 168.

In FIG. 5, LVS 156 is an invalid sense, not indicative of ventricular contraction. The invalidity of LVS 156 may not be evident from LVS 156 itself. A valid LVS is an intrinsic activation e.g., an activation generated in the Purkinje fibers of heart 12 that causes a ventricular contraction. The intrinsic activation spreads to both ventricles, and will be detected by pace/sense electrodes in both ventricles. In other words, when an intrinsic activation is sensed by LV pace/sense electrodes 20 and 22 and results in an LVS, the same activation will result in a RVS sensed by RV pace/sense electrodes 30 and 32.

Accordingly, the invention provides techniques for validating a LVS by checking for an occurrence of an RVS. The techniques carried out by pacemaker 10 may be executed by, for example, microprocessor 124 or pacer timing/control circuitry 136 or a dedicated processor not shown in FIG. 3 or 4.

When LVS 156 occurs, a special timing window commences. This timing window shall be called the "intrinsic inhibition window" (IIW). During the IIW, LV pacing is temporarily inhibited. The IIW in FIG. 5 is identified by reference numeral 170. If LVS 156 is a valid sense of intrinsic LV activity, then an RVS is expected to occur in IIW 170. Because no RVS is detected before IIW 170 expires, pacemaker 10 determines LVS 156 is invalid.

When an LVS such as LVS 156 is determined to be invalid, pacemaker 10 will not reset any intervals such as ventricular escape interval 166. From a pacing standpoint, LVS 156 is ignored. Pacemaker 10 may, however, record the occurrence of the invalid sense. When pacemaker 10 records an inordinate number of invalid LVS's, pacemaker 10 may respond by, for example, notifying the patient's physician that many LVS's are invalid. Pacemaker 10 may also automatically disable therapies that rely upon valid sensed events, such as correction of antidromic events, as will be described in connection with FIG. 12.

Figure 6:
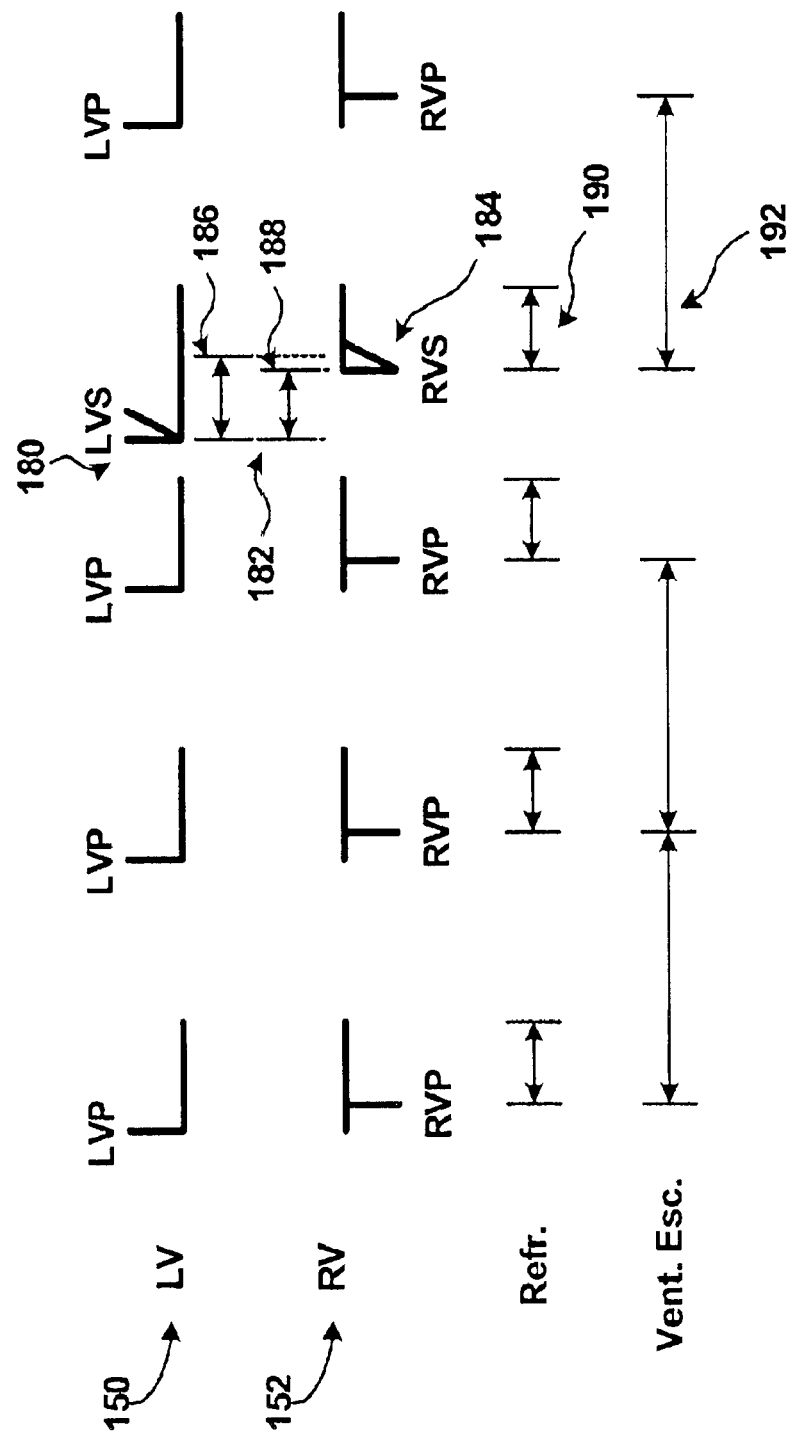
FIG. 6 is a timing diagram that illustrates a technique for recognition of a valid sense.

FIG. 6 is a timing diagram that illustrates techniques for recognition of a valid signal. FIG. 6 is similar to FIG. 5, including upper graph 150 of LV activity and lower graph 152 of RV activity. Like FIG. 5, LV activity includes paces and an LVS 180. Unlike LVS 156 in FIG. 5, LVS 180 is a valid signal.

When LVS 180 occurs, IIW 182 commences. Before IIW 182 expires, however, RVS 184 occurs. Because RVS 184 is detected before IIW 182 expires, pacemaker 10 determines LVS 180 is valid.

Detection of valid LVS 180 and RVS 184 cause pacemaker 10 to reset the pacing cycle. Because the ventricles have contracted in response to an intrinsic activation, LV and RV pacing is inhibited for this cardiac cycle. In addition, detection of RVS 184 causes pacemaker 10 to end IIW 182 early. Reference numeral 186 shows the maximum duration of IIW 182, and reference numeral 188 shows the actual duration of IIW 182. Furthermore, pacemaker 10 resets a refractory period 190 and a ventricular escape interval 192 to begin with RVS 184.

Figure 7:
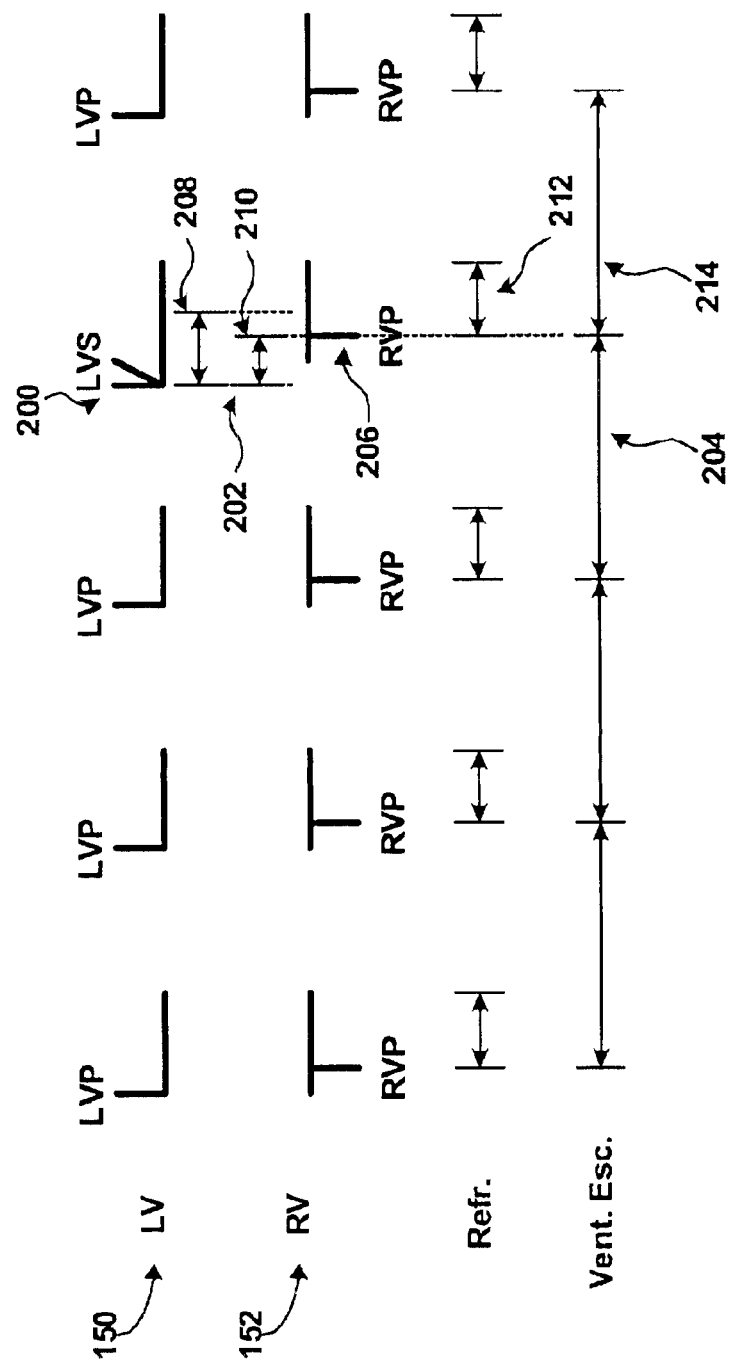
FIG. 7 is a timing diagram that illustrates a technique for responding to a sense that may be valid or invalid.

FIG. 7 is a timing diagram that illustrates another possible situation. In FIG. 7, LVS 200 occurs and IIW 202 commences. Before IIW 202 expires, however, escape interval 204 ends. In this situation, it may not be beneficial to the patient to wait and see whether an RVS will be detected in IIW 202. Instead of waiting for an RVS that might not occur at all, pacemaker 10 delivers RVP 206. When RVP 206 is delivered, pacemaker 10 cannot determine whether LVS 200 is valid or invalid.

Delivery of RVP 206 causes pacemaker 10 to reset the pacing cycle. Delivery of RVP 206 also causes pacemaker 10 to end IIW 202 early. Reference numeral 208 shows the maximum duration of IIW 202, and reference numeral 210 shows the actual duration of IIW 202. Furthermore, pacemaker 10 resets a refractory period 212 and a ventricular escape interval 214 beginning with RVP 206.

In FIG. 7, IIW 202 expires no later than escape interval 204 expires. If an RVS occurs before IIW 202 and escape interval 204 expire, then LVS 200 is a valid sense. Pacemaker 10 inhibits RV pacing for the cardiac cycle and resets the pacing cycle, as described above in connection with FIG. 6.

Figure 8:
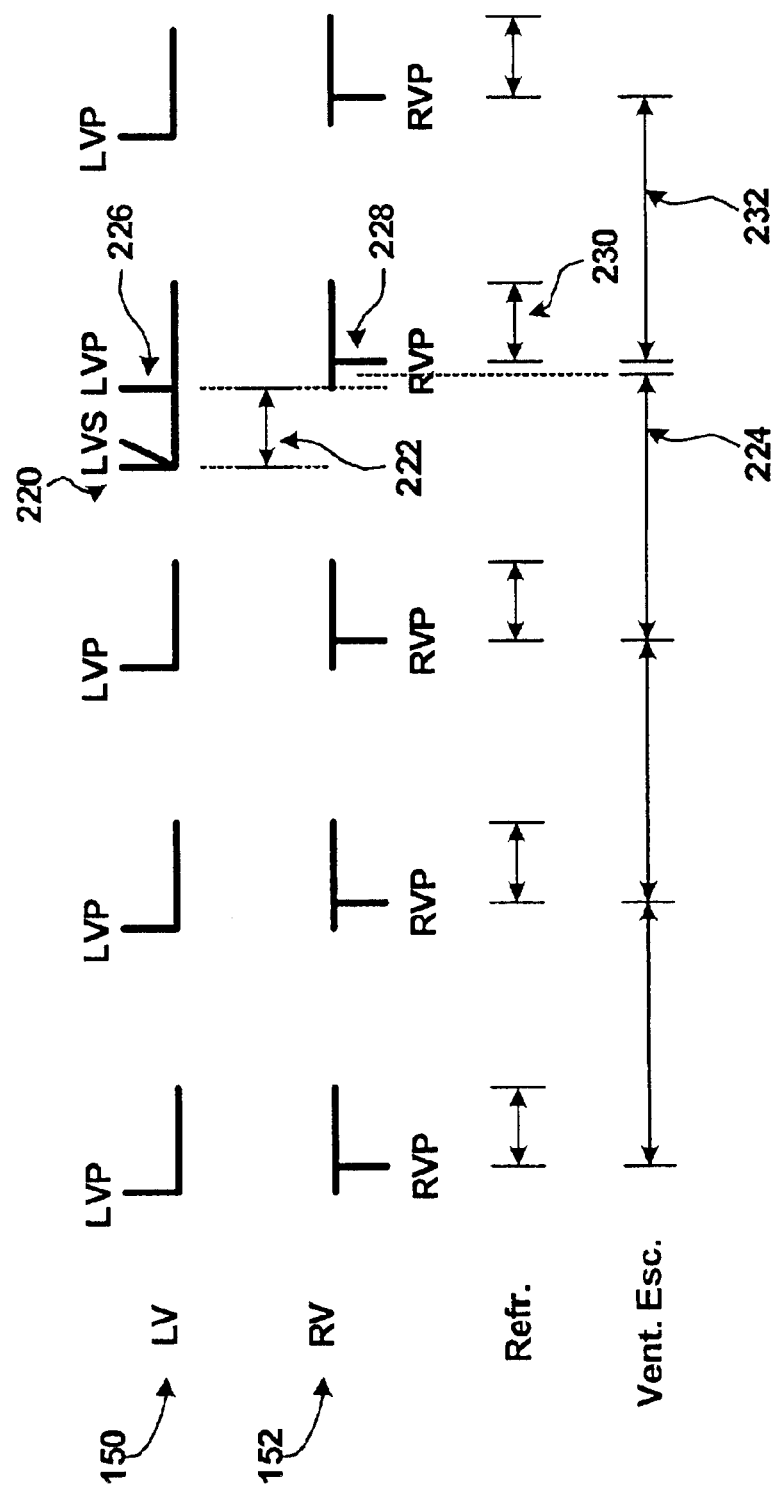
FIG. 8 is a timing diagram that illustrates another technique for responding to a sense that may be valid or invalid.

FIG. 8 is a timing diagram that illustrates another possible situation. In FIG. 8, LVS 220 occurs and IIW 222 commences. Unlike the timing shown in FIG. 7, escape interval 224 does not end in IIW 222. Unlike the timing shown in FIG. 5, an LVP would have taken place inside IIW 222, had the LVP not been inhibited. In this situation, very little time remains in IIW 222. Rather than pace the heart as in FIG. 7, it does little harm to wait and see whether LVS 220 is valid.

In FIG. 8, LVS 220 is invalid. No RVS occurs in IIW 222. Accordingly, when IIW 222 expires, pacemaker delivers LVP 226, followed by RVP 228. Pacemaker 10 resets the pacing cycle with respect to RVP 228, restarting a refractory period 230 and a ventricular escape interval 232. Pacemaker 10 may also record the occurrence of the invalid LVS 220.

Figure 9:
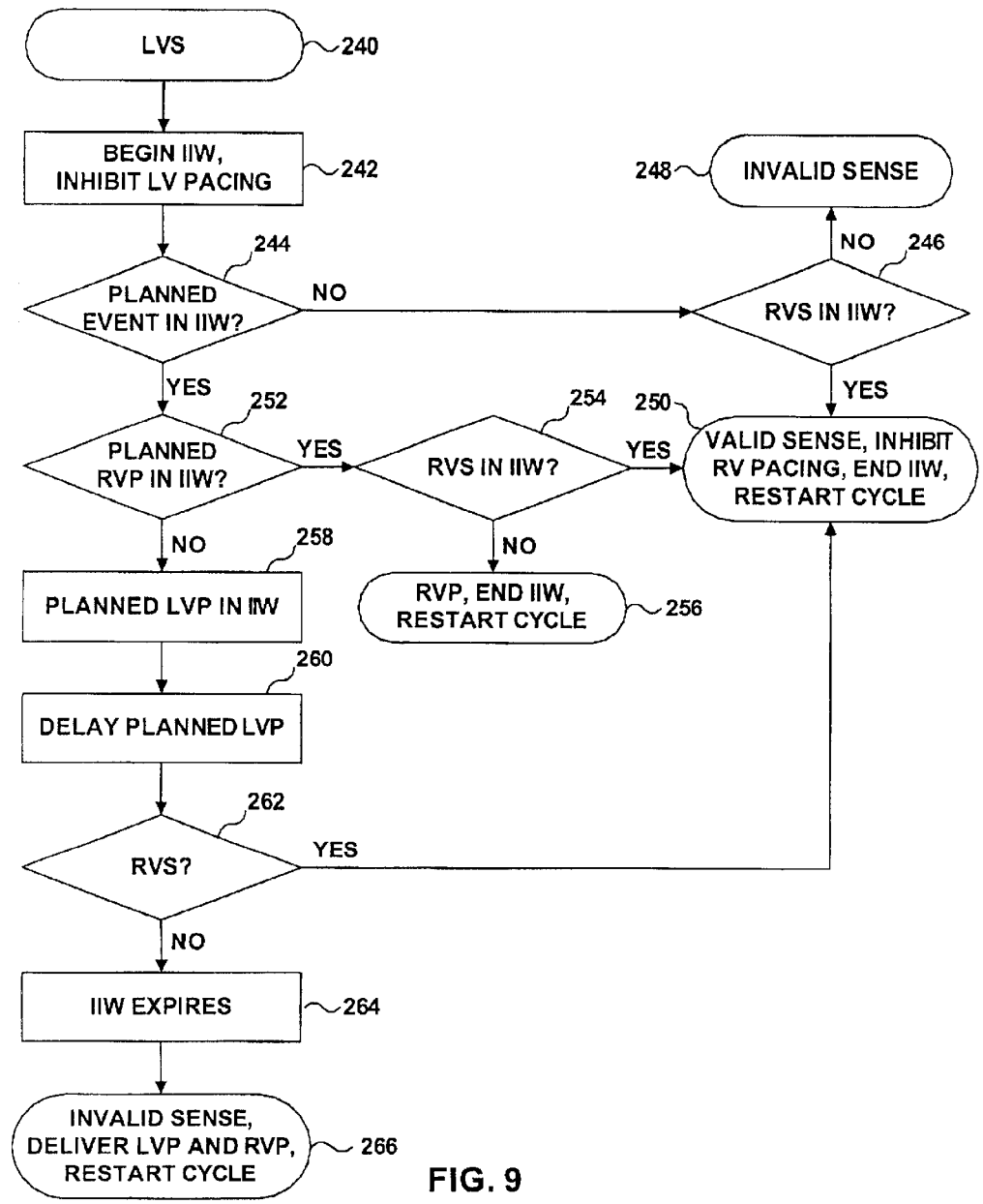
FIG. 9 is a flow diagram that illustrates techniques for responding to a sense that may be valid or invalid, including techniques illustrated in FIGS. 5–8.

The techniques illustrated in FIGS. 5-8 are summarized in the flow diagram in FIG. 9. When an LVS occurs (240), pacemaker 10 begins an IIW (242). During the IIW, LV pacing is inhibited. Pacemaker 10 may begin the IIW by, for example, resetting a digital timer or counter that controls the IIW. By sensing the counter that controls the IIW, the counter that controls the ventricular escape interval and the counter that controls the delay between LV and RV pacing pulses, pacemaker 10 can determine whether an event such as a planned RVP is expected to take place in the IIW (244). When no events are planned to take place in the IIW, pacemaker 10 waits to see whether RV pace/sense electrodes 30 and 32 detect an RVS (246). If no RVS occurs in the IIW (246), then the LVS is invalid (248). This situation is illustrated in FIG. 5.

When an LVS is invalid (248), the LVS is ignored from a pacing standpoint. The invalid LVS does not restart timing cycles. Pacemaker 10 may, however, record the occurrence of the invalid sense. As noted above and as described below in connection with FIG. 12, an inordinate number of invalid LVS's may invoke a response from pacemaker 10.

If an RVS occurs in the IIW (246), then the LVS is valid (250). When the LVS is valid, pacemaker 10 inhibits LV and RV pacing for the cardiac cycle. Pacemaker 10 further ends the IIW and restarts the cardiac cycle by resetting a refractory period and a ventricular escape interval. This situation is illustrated in FIG. 6.

When pacemaker 10 determines that an event is expected to take place in the IIW (244), the event could be an RVP (252). In other words, the ventricular escape interval is expected to end in the IIW. In this situation, the IIW ends no later than the time the ventricular escape interval ends. If an RVS occurs before the IIW and the ventricular escape interval expire (254), then the LVS is valid (250). Otherwise, the RVP is delivered when the escape interval expires (256). Delivery of the RVP causes pacemaker 10 to reset the pacing cycle, as described above. This situation is illustrated, without the occurrence of an RVS, in FIG. 8.

When the ventricular escape interval will not end in the IIW, but an LVP would occur in the IIW but for the inhibition (258), then the LVP is delayed for the pending cardiac cycle until the IIW expires (260). If an RVS occurs in the IIW (262), then the LVS is valid (250). Otherwise, the IIW expires (264), and an LVP and RVP are delivered (266). Pacemaker 10 resets the pacing cycle, as described above, and may record the LVS as invalid. This situation is illustrated, without the occurrence of an RVS, in FIG. 8.

Although the techniques shown in FIGS. 5–9 show a patient with a positive LV-RV delay, the techniques may be adapted for a patient with a negative LV-RV delay.

The duration of an IIW may vary from patient to patient. Rarely will an IIW exceed 200 milliseconds. Typical IIW's may last from 70 milliseconds to 120 milliseconds, but IIW's for particular patents may be shorter or longer.

In some patients, for example, intrinsic activations may originate from a region in heart 12 approximately equidistant from LV pace/sense electrodes 20 and 22 and RV pace/sense electrodes 30 and 32. The activation may reach LV pace/sense electrodes 20 and 22 and RV pace/sense electrodes 30 and 32 at nearly the same time. In these patients, the IIW may be of short duration, because a valid LVS would be expected to be followed by an RVS very quickly. In other patients, intrinsic activations are more likely to reach one set of electrodes before reaching another. In these patients, the IIW may be of a longer duration.

Figure 10:
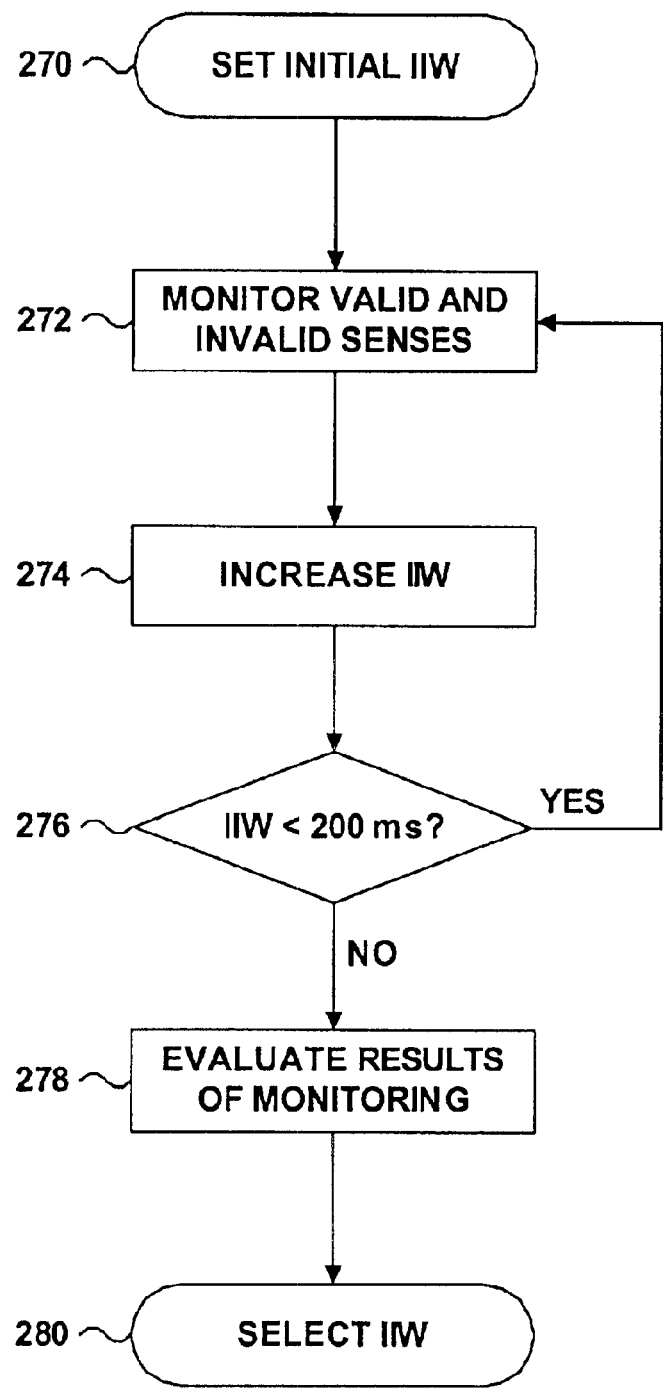
FIG. 10 is a flow diagram that illustrates a technique for selection of an intrinsic inhibition window.

FIG. 10 is a flow diagram illustrating a technique for setting an IIW for a patient. Beginning with a narrow IIW (270), such as an IIW at or near zero, pacemaker 10 monitors valid and invalid senses (272). Monitoring may include, for example, recording with a counter the number of invalid senses for the IIW and recording with another counter the number of all senses. After a period of monitoring, the IIW is widened (274) by, for example, 10 milliseconds. Pacemaker 10 monitors valid and invalid senses for the new IIW (272). Because an IIW will rarely exceed 200 milliseconds, monitoring may discontinue when the IIW exceeds 200 milliseconds (276).

Once monitoring has been discontinued, pacemaker 10 may evaluate the results of monitoring (278). By considering the number of invalid senses in comparison to the total senses for each IIW, an IIW may be selected (280). For most patients, the percentage of invalid senses starts high when the IIW is narrow, and drops as the IIW expands. In general, pacemaker 10 selects an IIW that is wide enough to detect valid senses, i.e., pacemaker 10 selects an IIW that is wide enough that intrinsic activations are likely to be sensed at LV pace/sense electrodes 20 and 22 and at RV pace/sense electrodes 30 and 32 within the IIW.

The procedure shown in FIG. 10 is merely an exemplary procedure for setting the IIW. The procedure may be modified by, for example, beginning with a wide IIW of 200 milliseconds and narrowing the IIW after a period of monitoring. In addition, it may not be necessary to wait until all monitoring is completed before evaluating the results. The results may be evaluated after each period of monitoring, and monitoring may be terminated when further expanding the IIW produces no discernable benefit.

Figure 11:
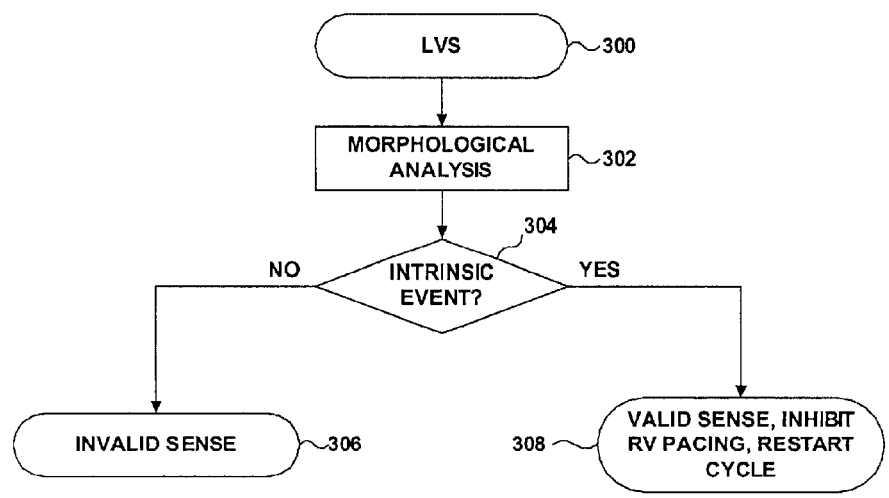
FIG. 11 is a flow diagram that illustrates a technique for recognition of valid and invalid senses with morphological analysis.

FIG. 11 is a flow diagram illustrating an additional embodiment of the invention. This embodiment employs morphological analysis as a supplement to, or as a substitute for, an IIW. As noted above, pacemaker 10 may digitally analyze signals sensed by electrodes 20, 22, 30 and 32. Signals from selected electrodes are provided to multiplexer 128, and are converted to multi-bit digital signals by A/D converter 130. Microprocessor 124 may employ digital signal analysis techniques to analyze the digitized signals.

Digital analysis may include any of a number of morphological techniques that analyze the shape of the signal. A signal caused by a myopotential, for example, may have a shape that is distinguishable from the shape of a signal caused by an intrinsic activation. Morphological analysis may be used as an additional tool for distinguishing valid senses from invalid senses.

Morphological analysis includes any of several techniques that distinguish one shape from another. Such techniques may include, for example, Fourier analysis, wavelet analysis, adaptive filter analysis and morphological template matching.

When an LVS occurs (300), pacemaker 10 performs a morphological analysis (302). Based upon the shape of the signal that resulted in the LVS, pacemaker 10 may determine whether the LVS resulted from an intrinsic event (304), i.e., whether the LVS resulted from electrical activity in the left ventricle. If the LVS resulted from an intrinsic event, the LVS is valid, otherwise the LVS is invalid. If the LVS is invalid, the sense is ignored and may be recorded as an invalid sense (306). If the sense is valid, pacing may be inhibited and the pacing cycle may be restarted (308).

The techniques shown in FIG. 9 and the techniques shown in FIG. 11 are not exclusive of each other. Pacemaker 10 may use both timing-related techniques and morphological techniques to distinguish valid senses from invalid senses.

Figure 12:
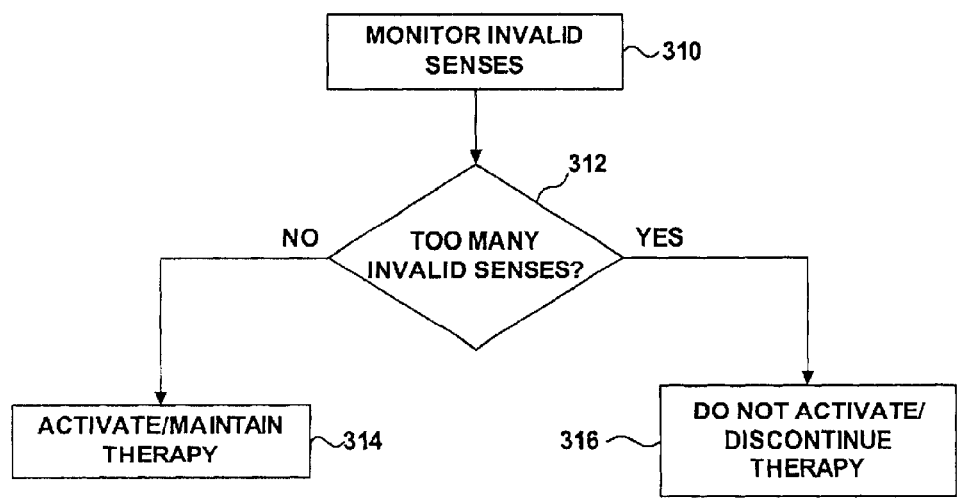
FIG. 12 is a flow diagram that illustrates techniques for adjusting therapy as a function of valid and invalid senses.

FIG. 12 is a flow diagram illustrating a further embodiment of the invention. Some therapies, such as correction of antidromic events, use senses to trigger the therapy. It is undesirable to trigger therapy upon an invalid sense. The occurrence of too many invalid senses may result in too many "false alarms," with therapy being provided that is not beneficial or that may be harmful.

Pacemaker 10 therefore monitors senses such as LVS's for a monitoring period (310), and evaluates whether there are inordinate number of invalid senses (312). If there are comparatively few or no invalid senses, pacemaker 10 may activate the sense-based therapy, or if the therapy is already activated, may maintain the therapy (314). If there are too many invalid senses, however, pacemaker 10 may inhibit activation of the sense-based therapy, or if the therapy is already activated, may disable or discontinue the therapy (316).

Figure 13:
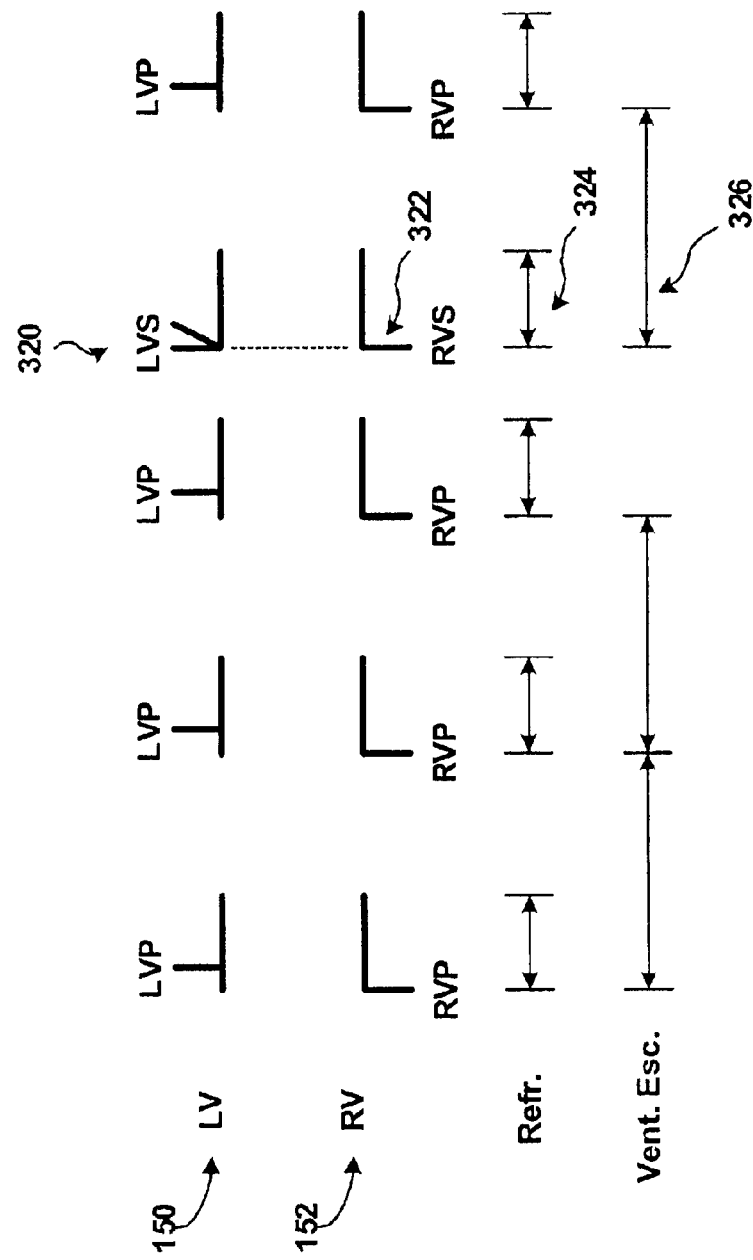
FIG. 13 is a timing diagram that illustrates treatment of an antidromic event.

FIG. 13 is a timing diagram that illustrates a technique for correction of antidromic events. The timing diagram shows that the patient is being paced with a negative LV-RV delay. In this patient, intrinsic activity that causes the left ventricle to beat before the right ventricle is undesirable.

The patient experiences an antidromic event when an intrinsic LVS 320 occurs prior to RV activation. In response to the antidromic event, pacemaker 10 compensates by delivering a RVP 322 when LVS 320 is sensed. RVP 322 is delivered immediately. As a result, the ventricles contract nearly simultaneously, which is generally better for the patient than having the ventricles contract out of order. Pacemaker 10 also resets the pacing cycle with respect to RVP 322, restarting a refractory period 324 and a ventricular escape interval 326.

The therapy for a patient paced with a positive LV-RV delay is similar to that shown in FIG. 13. The patient experiences an antidromic event when an intrinsic RVS occurs prior to LV activation. Pacemaker 10 compensates by delivering an LVP when the RVS is sensed, causing the ventricles contract nearly simultaneously.

As shown in FIG. 13, therapy for antidromic events is a sense-based therapy, i.e., delivery of therapy is triggered by senses. For the therapy to be effective, the triggering senses should be valid. LVS 320 is assumed to be a valid sense, and RVP 322 follows LVS 320 immediately. Therapy for antidromic events is one example of a therapy that may be activated or inhibited following monitoring as shown in FIG. 12. When the results of monitoring show comparatively few or no invalid senses, pacemaker 10 may activate the therapy for antidromic events shown in FIG. 13.

The invention offers several advantages. The use of a timing window represents a simple technique for distinguish a valid cardiac sense from an invalid one. The senses in question may be detected by any cardiac electrode, and checked by another electrode positioned to detect intrinsic activity. Although described in the context of an LV pace/sense electrode, the techniques of the invention may be applied to the RV pace/sense electrode, or to pace/sense electrodes disposed proximal to the atria.

Moreover, use of a timing window is not computationally demanding and does not interfere with other pacing operations. Morphological analysis, which is more computationally demanding than use of a timing window, may be also be used to supplement or supplant use of the timing window. In some patients, the timing window will provide sufficient distinction of valid and invalid senses. The timing window can be customized to the patient using the techniques described above. Data pertaining to valid and invalid senses may be used by pacemaker 10 to automatically regulate therapies that rely on valid senses.

The preceding specific embodiments are illustrative of the practice of the invention. It is to be understood, therefore, that other expedients known to those skilled in the art or disclosed herein may be employed without departing from the invention or the scope of the claims. For example, the invention is useful in bi-ventricular pacemakers, but the invention is not limited to that context. The techniques of the invention may be applied, for example, to evaluate the validity of atrial senses.

Furthermore, the invention is not limited to evaluating the validity of LVS's. In some patients, the LVS may be reliable but the RVS may be suspect. The techniques of the invention may be applied to evaluate the validity of RVS's.

The invention further includes within its scope the methods of making and using the systems described above. These methods are not limited to the specific examples described above, but may be adapted to meet the needs of a particular patient. The invention also includes within its scope any of computer-readable media comprising instructions for causing a programmable processor, such as microprocessor 24, to carry out the techniques described above. These and other embodiments are within the scope of the following claims.

In the claims, means-plus-functions clauses are intended to cover the recited structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. A method comprising:
   sensing an electrical signal with a first electrode;
   commencing a timing window;
   inhibiting delivery of a pacing therapy by the first electrode subsequent to termination of an escape interval during the timing window; and
   recording the electrical signal as an invalid sense when a second electrode fails to sense the electrical signal in the timing window.

2. A method of claim 1, further comprising:
   ending the timing window; and
   resetting an escape interval when the second electrode senses the electrical signal in the timing window.

3. The method of claim 2, wherein the second electrode senses the electrical signal in the timing window.

4. The method of claim 1, wherein the first electrode is the a left ventricular electrode and the second electrode is a right ventricular electrode.

5. The method claim 1, further comprising:
   performing a morphological analysis of the electrical signal; and
   recording the electrical signal as an invalid sense as a function of the morphological analysis.

6. The method of claim 1, further comprising counting the number of invalid senses during a monitoring period.

7. The method of claim 6, further comprising adjusting therapy as a function of the number of invalid senses during the monitoring period.

8. The method of claim 1, wherein inhibiting delivery of a pacing therapy comprises:
   determining whether termination of the escape interval occurs a predetermined time period prior to expiration of the timing window;
   inhibiting delivery of the pacing therapy in response to termination of the escape interval occurring within the predetermined time period; and
   delivering the pacing therapy in response to termination of the escape interval not occurring within the predetermined time period.

9. A computer-readable medium comprising instructions for causing a programmable processor to:
   sense a electrical signal with a first electrode;
   commence a timing window;
   inhibit delivery of a pacing therapy by the first electrode subsequent to termination of an escape interval during the timing window; and
   record the electrical signal as an invalid sense when a second electrode fails to sense the electrical signal in the timing window.

10. The medium of claim 9, the instructions further causing the programmable processor to:
end the timing window; and
reset an escape window when the second electrode senses the electrical signal in the timing window.

11. The medium of claim 10, wherein the second electrode delivers pacing therapy, the instructions further causing the programmable processor to inhibit pacing therapy with the second electrode until the expiration of the reset escape interval.

12. The medium of claim 9, wherein the first electrode is a left ventricular electrode and the second electrode is a right ventricular electrode.

13. The medium of claim 9, the instructions further causing the programmable processor to:
perform a morphological analysis of the electrical signal; and
record the electrical signal as an invalid sense as a function of the morphological analysis.

14. The medium of claim 9, the instructions further causing the programmable processor to count the number of invalid senses during a monitoring period.

15. The medium of claim 14, the instructions further causing the programmable processor to adjust therapy as a function of the number of invalid senses during the monitoring period.

16. A method comprising:
sensing an electrical signal with a left ventricular electrode;
commencing a timing window;
inhibiting delivery of a pacing therapy by the left ventricular electrode subsequent to termination of an escape interval during the timing window; and
recording the electrical signal as an invalid sense when a right ventricular electrode fails to sense the electrical signal in the timing window.

17. The method of claim 16, further comprising:
sensing the electrical signal with the right ventricular electrode in the timing window;
ending the timing window;
resetting an escape interval; and
inhibiting pacing with the right ventricular electrode until the expiration of the reset escape interval.

18. The method of claim 16, further comprising ending the timing window and delivering a right ventricular pace when a ventricular escape interval expires in the timing window.

19. The method of claim 16, further comprising delivering a left ventricular pace and a right ventricular pace after the timing window expires.

20. The method claim 19, further comprising:
delivering the left ventricular pace immediately after the timing window expires.

21. A system comprising:
a first electrode for placement proximal to a heart;
a second electrode for placement proximal to the heart;
a controller that senses an electrical signal as an invalid sense when the controller fails to sense the electrical signal with the second electrode in a timing window, wherein the controller inhibits delivery of a pacing therapy by the first electrode subsequent to termination of an escape interval during the timing window.

22. The system of claim 21, wherein the controller ends the timing window and resets an escape interval when the controller senses the electrical signal with the second electrode in the timing window.

23. The system of claim 21, wherein the controller counts the number of invalid senses during a monitoring period.

24. The system of claim 23, wherein the controller adjusts therapy as a function of the number of invalid senses during the monitoring period.

25. The system of claim 21, wherein the controller performs a morphological analysis of the electrical signal.

26. The system of claim 21, wherein the first electrode is a left ventricular electrode and the second electrode is a right ventricular electrode.

27. The system of claim 26, wherein the controller delivers a right ventricular pace and a left ventricular pace after the timing window expires.

28. The system of claim 21, wherein the controller comprises a microprocessor.

29. The system of claim 21, wherein the controller determines whether termination of the escape interval occurs a predetermined time period prior to expiration of the timing window, inhibits delivery of the pacing therapy in response to termination of the escape interval occurring within the predetermined time period, and delivers the pacing therapy in response to termination of the escape interval not occurring within the predetermined time period.

30. A method comprising:
in a first monitoring period,
sensing at least one electrical signal with a first electrode,
commencing a timing window having a first duration and
recording the electrical signal as an invalid sense when a second electrode fails to sense the electrical signal in the timing window having the first duration; and
in a second monitoring period,
sensing at least one electrical signal with the first electrode,
commencing a timing window having a second duration.

31. The method of claim 30, further comprising recording the electrical signal as a valid sense in the first monitoring period when the second electrode senses the electrical signal in the timing window having the first duration.

32. The method claim 30, further comprising:
incrementing a counter for each electrical signal sensed with the first electrode in the first monitoring period.

33. The method of claim 32, further comprising:
resetting the counter;
incrementing the counter for each electrical signal sensed with the first electrode in the second monitoring period.

34. The method of claim 30, further comprising selecting a timing window duration as a function of the invalid senses in the first monitoring period and the second monitoring period.

35. A method comprising:
sensing an electrical signal with a first electrode;
commencing a timing window;
inhibiting delivery of a pacing therapy by the first electrode subsequent to termination of an escape interval during the timing window; and
recording the electrical signal as a valid sense when a second electrode senses the electrical signal in the timing window.

36. The method claim 35, further comprising recording the electrical signal as an invalid sense when a second electrode fails to sense the electrical signal in the timing window.

37. The method of claim 35, further comprising ending the timing window and resetting an escape interval when the second electrode senses the electrical signal in the timing window.

38. The method of claim 35, wherein the first electrode is a left ventricular electrode and the second electrode is a right ventricular electrode.

39. The method of claim 35, further comprising:
performing a morphological analysis of the electrical signal; and
recording the electrical signal as a valid sense as a function of the morphological analysis.

40. The method of claim 35, further comprising counting the number of total electrical signals sensed with the first electrode during a monitoring period.

41. A computer-readable medium comprising instructions for causing a programmable processor to:
sense an electrical signal with a first electrode;
commence a timing window;
inhibiting delivery of a pacing therapy by the first electrode subsequent to termination of an escape interval during the timing window; and
record the electrical signal as a valid sense when a second electrode senses the electrical signal in the timing window.

42. The medium of claim 41, the instructions further causing the programmable processor to record the electrical signal as an invalid sense when a second electrode fails to sense the electrical signal in the timing window.

43. The medium of claim 41, the instructions further causing the programmable processor to end the timing window and reset an escape interval when the second electrode senses the electrical signal in the timing window.

44. The medium of claim 41, wherein the first electrode is a left ventricular electrode and the second electrode is a right ventricular electrode.

45. The medium of claim 41, the instructions further causing the programmable processor to:
perform a morphological analysis of the electrical signal; and
record the electrical signal as a valid sense as a function of the morphological analysis.

46. The medium of claim 41, the instructions further causing the programmable processor to count the number of total electrical signals sensed with the first electrode during a monitoring period.

47. A system comprising:
a first sensing means for placement proximal to a heart;
a second sensing means for placement proximal to the heart;
a therapy delivery means for delivering therapy to the heart; and
a controlling means for sensing an electrical signal with the first sensing means, commencing a timing window, inhibiting delivery of a pacing therapy by the therapy delivery means subsequent to termination of an escape interval during the timing window, and recording the electrical signal as an invalid sense when the controller fails to sense the electrical signal with the second sensing means in the timing window.

48. The system of claim 47, wherein the controller means ends the timing window and resets an escape interval when the controller senses the electrical signal with the second sensing means in the timing window.

49. The system of claim 47, wherein the controller means counts the number of invalid senses during a monitoring period and adjusts therapy as a function of the number of invalid senses during the monitoring period.

50. The system of claim 47, wherein the controller means performs a morphological analysis of the electrical signal.

51. The system of claim 50, wherein the controller means includes a means for converting the electrical signal to a digital signal.

52. The system of claim 47, wherein the controller means comprises a microprocessor.

53. The system of claim 47, wherein the controller means comprises a sense amplifier means for providing a sensing threshold as a function of the measured amplitude of the electrical signal.

* * * * *